US008147815B2

(12) United States Patent
Malek

(10) Patent No.: US 8,147,815 B2
(45) Date of Patent: *Apr. 3, 2012

(54) TOPICAL ADMINISTRATION CARRIER COMPOSITION AND THERAPEUTIC FORMULATIONS COMPRISING SAME

(75) Inventor: Shane Malek, Las Vegas, NV (US)

(73) Assignee: Celmatrix Corporation, Las Vegas, NV (US)

( * ) Notice: Subject to any disclaimer, the term of this patent is extended or adjusted under 35 U.S.C. 154(b) by 553 days.

This patent is subject to a terminal disclaimer.

(21) Appl. No.: 11/305,647

(22) Filed: Dec. 16, 2005

(65) Prior Publication Data

US 2007/0141004 A1    Jun. 21, 2007

(51) Int. Cl.
*A61K 31/132* (2006.01)
*A61K 8/00* (2006.01)

(52) U.S. Cl. ..................... 424/70.31; 424/401

(58) Field of Classification Search .......................... None
See application file for complete search history.

(56) References Cited

U.S. PATENT DOCUMENTS

| | | | |
|---|---|---|---|
| 3,215,602 A * | 11/1965 | Diamond | 514/474 |
| 3,306,824 A * | 2/1967 | Laasko et al. | 424/673 |
| 3,317,380 A * | 5/1967 | Veldkamp | 514/428 |
| 3,427,382 A | 2/1969 | Haefele | |
| 3,729,568 A | 4/1973 | Kligman | |
| 4,021,574 A | 5/1977 | Bollag et al. | |
| 4,034,114 A | 7/1977 | Yu et al. | |
| 4,139,619 A | 2/1979 | Chidsey, III | |
| 4,170,229 A | 10/1979 | Olson | |
| 4,185,099 A | 1/1980 | Sorbini | |
| 4,201,235 A | 5/1980 | Ciavatta | |
| 4,405,525 A * | 9/1983 | Knight et al. | 552/530 |
| 4,820,512 A | 4/1989 | Grollier | |
| 4,855,294 A | 8/1989 | Patel et al. | |
| 5,030,442 A | 7/1991 | Uster et al. | |
| 5,183,817 A | 2/1993 | Bazzano | |
| 5,270,035 A * | 12/1993 | Chimento | 424/70.8 |
| 5,514,672 A | 5/1996 | Bazzano | |
| 5,733,572 A | 3/1998 | Unger et al. | |
| 5,750,108 A | 5/1998 | Edwards | |
| 5,800,807 A * | 9/1998 | Hu et al. | 424/78.04 |
| 5,824,295 A | 10/1998 | Syed et al. | |
| 5,843,415 A | 12/1998 | Klar | |
| 5,853,706 A | 12/1998 | Klar | |
| 5,917,021 A * | 6/1999 | Lee | 530/387.3 |
| 5,951,991 A | 9/1999 | Wagner et al. | |
| 5,972,345 A | 10/1999 | Chizick et al. | |
| 6,156,295 A | 12/2000 | Shah | |
| 6,255,313 B1 | 7/2001 | Suzuki et al. | |
| 6,284,234 B1 | 9/2001 | Niemiec et al. | |
| 6,379,688 B2 * | 4/2002 | Yamaguchi et al. | 424/406 |
| 6,589,514 B2 | 7/2003 | Jensen et al. | |
| 6,596,266 B2 | 7/2003 | Catalfo et al. | |
| 6,723,309 B1 | 4/2004 | Deane | |
| 6,946,120 B2 | 9/2005 | Wai-Chiu So et al. | |
| 2001/0031286 A1 | 10/2001 | Porras et al. | |
| 2002/0009423 A1 | 1/2002 | Murad | |
| 2002/0048558 A1 * | 4/2002 | Niemiec et al. | 424/70.22 |
| 2002/0053537 A1 * | 5/2002 | Lucido et al. | 210/94 |
| 2003/0007941 A1 * | 1/2003 | Cornelius et al. | 424/70.1 |
| 2003/0053971 A1 | 3/2003 | Carson et al. | |
| 2003/0077297 A1 | 4/2003 | Chen et al. | |
| 2003/0092754 A1 * | 5/2003 | Nishimuta et al. | 514/398 |
| 2003/0199644 A1 * | 10/2003 | Kim et al. | 525/453 |
| 2004/0141935 A1 | 7/2004 | Styczynski et al. | |
| 2004/0157766 A1 * | 8/2004 | Embil et al. | 514/1 |
| 2004/0204433 A1 | 10/2004 | Imamura et al. | |
| 2004/0254252 A1 * | 12/2004 | Engles et al. | 514/699 |
| 2005/0049232 A1 | 3/2005 | Lindau | |
| 2005/0079139 A1 | 4/2005 | Jacques et al. | |
| 2005/0163811 A1 | 7/2005 | Lee et al. | |
| 2005/0186164 A1 | 8/2005 | Akyuz | |
| 2005/0238675 A1 * | 10/2005 | Li et al. | 424/400 |
| 2007/0141015 A1 * | 6/2007 | Malek | 424/70.31 |

FOREIGN PATENT DOCUMENTS

| | | |
|---|---|---|
| WO | WO-97/02041 A1 | 1/1997 |
| WO | WO-02/11698 A1 | 2/2002 |

OTHER PUBLICATIONS

Fisher, A.A.; Cutis, 1990, 45(2), pp. 81-82.*
Olsen et al., J. Am. Acad. Dermatol., 2002, 47(3), pp. 377-385.*
Rook, Arthur, Some chemical influences on hair growth and pigmentation, Brit. J. Derm., Mar. 1965, pp. 115-129, vol. 77, No. 3.
Sawaya, Marty E., Novel agents for the treatment of alopecia, Seminars in Cutaneous Medicine and Surgery, Dec. 1998, pp. 276-283, vol. 17, No. 4.
Dethlefs, J., et al., "Zur wirking einer vitamin-aminosaure-kombination auf das haarwachstum", "Z. Allgemeinmedzin (German)", 1977, pp. 684-688, vol. 12.
Dethlefs, J., et al., "Effect of a combination of vitamin and amino acid on the hair growth," English Translation of Abstract, "Z. Allgemeinmedzin (German)", 1977, pp. 684-688, vol. 12.
Much, T., "Treatment of alopecia areata with vitamin A acid", "Z. Hautkr. (German)," English Translation of Abstract, Dec. 1, 1976, pp. 993-998, vol. 51, No. 23.
Much, T., "Treatment of alopecia areata with vitamin A acid", "Z. Hautkr. (German)", Dec. 1, 1976, pp. 993-998, vol. 51, No. 23.
Olsen, E. et al., "A randomized clinical trial of 5% topical minoxidil versus 2% topical minoxidil and placebo in the treatment of androgenetic alopecia in men", "Journal of Am. Academy of Dermatology", Sep. 2002, pp. 377-385, vol. 47, No. 3.

* cited by examiner

*Primary Examiner* — Brian Gulledge
(74) *Attorney, Agent, or Firm* — Hultquist, PLLC; Mary Grant; Steven Hultquist

(57) ABSTRACT

A topical administration carrier composition including water, glycerin and polysorbate, suitable for use with compositions containing active ingredients such as minoxidil that are susceptible to volatilization and transdermal penetration in application to the body. The carrier formulation retards the evaporative and systemic migration losses of the active ingredient composition, to provide sustained topical action, in relation to formulations lacking the components of the inventive composition.

2 Claims, No Drawings

TOPICAL ADMINISTRATION CARRIER COMPOSITION AND THERAPEUTIC FORMULATIONS COMPRISING SAME

FIELD OF THE INVENTION

The present invention relates to topical administration carrier compositions for use in preparing formulations including therapeutic agents and other active ingredients, for administration to scalp, skin and other topical areas of the body.

BACKGROUND OF THE INVENTION

In the formulation of carriers for topical administration of therapeutic agents and other active ingredients, a wide variety of formulation components are employed, which are in many cases specifically adapted to the particular active ingredient to be applied.

A significant problem in the topical administration of many active ingredient compositions is that they are highly volatile in character. In consequence, evaporative losses of the active ingredient compositions are significant, and result in diminution of the treatment efficacy of such ingredient compositions. Evaporative loss of the active ingredient compositions therefore may severely diminish the therapeutic effect and/or duration of benefit of the active ingredient on the areas of the body to which the formulation has been topically applied.

As a result, increased amounts of the topical composition may need to be applied, to ensure the beneficial effect. This may in turn lead to gross overuse of the composition, in an effort to provide surplus material to compensate for evaporative losses of the active ingredient composition.

Another problem that frequently occurs in use of topical compositions, e.g., skin treatments, hair treatments, hair growth compositions, cuticle treatments, and the like, is that the active ingredient may be highly susceptible to systemic migration. By systemic migration is meant that the active topical agent penetrates through the skin, hair, nails, etc. into the system of the user, with consequent loss of surface activity of the active ingredient(s). As in the case of evaporative loss, systemic migration diminishes the beneficial effect of the active ingredient, with the same consequences as those discussed above in respect of evaporative loss.

Additionally, such systemic migration may result in systemic toxicity effects deriving from the active ingredient(s) intended to remain on the surface of the skin, scalp, hair, etc., which nonetheless pass into the body through the skin, hair follicles, and/or other systemic portals, where the active ingredient is not desired and where it may in fact contribute to adverse physiological side-effects.

There is therefore a continuing effort in the field of topical compositions containing active ingredients susceptible to such deficiencies to develop improved compositions that retard evaporative loss and systemic penetration of active ingredients.

SUMMARY OF THE INVENTION

The present invention relates to topical administration carrier compositions that are usefully employed in preparing formulations of active ingredients for topical administration to the body, e.g., to the skin, hair, etc.

The present invention relates to a topical administration carrier composition suitable for use with active ingredient compositions that are susceptible to evaporative loss and systemic migration when topically applied to the body.

The topical administration carrier composition contains as ingredients water, glycerin and polysorbate, in relative proportions to one another that reduce the evaporative loss and systemic migration that would otherwise occur in the absence of such carrier. The topical administration carrier composition can alternatively consist, or consist essentially of, such ingredients.

The invention relates in one aspect to a carrier formulation consisting essentially of water, glycerin and retinol, in relative proportions to one another so that the formulation retards volatilization and transdermal penetration of topically active agent compositions otherwise susceptible to evaporative loss and transdermal systemic migration.

In a further aspect, the invention relates to a carrier composition, comprising:
from 20 to 60 weight percent water;
from 6 to 20 weight percent glycerin; and
from 5-15 weight percent polysorbate.

A further aspect of the invention relates to a method of formulating a topical composition containing at least one active ingredient that is susceptible to evaporative loss and undesired systemic penetration from a topical locus, such method comprising incorporating the active ingredient(s) in a composition including the carrier composition.

Additional objects, features and advantages of the invention will be readily apparent from the description that follows, and readily derivable by empirical determination without undue effort, based on the description herein.

DETAILED DESCRIPTION OF THE INVENTION, AND PREFERRED EMBODIMENTS THEREOF

The present invention relates to a topical administration carrier composition suitable for use with active ingredients ingredient compositions that are susceptible to evaporative loss and systemic migration when topically applied to the body.

The topical administration carrier composition contains as ingredients water, glycerin and polysorbate, in relative proportions to one another that reduce the evaporative loss and systemic migration that would otherwise occur in the absence of such carrier. The topical administration carrier composition can alternatively consist, or consist essentially of, such ingredients.

The invention therefore provides a simple and effective carrier composition that has been found to be highly effective in application to active ingredient compositions such as hair growth promoters, and such carrier position has particular applicability for active ingredients such as minoxidil, to retard evaporative loss and systemic migration from the scalp areas to which the formulation is applied.

In one embodiment, the carrier composition of the invention consists essentially of water, glycerin and polysorbate-80, e.g., in amounts of:
50-75 weight percent water;
20-40 weight percent glycerin; and
5-15 weight percent polysorbate-80
wherein the weight percents of such ingredients are based on the total weight of the carrier composition and the weight percentages of all components total to 100 weight percent.

In a specific embodiment of such carrier composition, the composition may be formulated with additional optional ingredients, including, for example, panthenol, cysteine, 3-betasitosterol, 4-retinol, biotin, flavorants such as fruit extracts, syrups, and the like, preservatives (e.g., methylparabin), DMDM hydantoin, polysorbate-20 (as an adjuvant stabilizer for retinol, when retinol is present in the composition), and the like.

In a specific formulation, the topical carrier composition includes the following ingredients:
- 65-70 weight percent water;
- 30-35 weight percent glycerin; and
- 0.1-5 weight percent polysorbate-80 wherein the total weight percentages of such essential components totals to 100 weight percent.

In various other carrier compositions of the invention, water is present in an amount of 60-72 weight percent, glycerin is present in an amount of from 28-30 weight percent, and polysorbate-80 is present is an amount of from 0.05-1.5 weight percent.

It will be recognized that essential ingredients of the compositions of the invention can be varied in relative proportions to one another, and that various formulations can be made up, as appropriate to specific active ingredient(s) to be utilized with the carrier for topical use.

As mentioned, the carrier of the present invention can consist, or consist essentially of, the water, glycerin and polysorbate components described hereinabove as essential components of such carrier composition.

In further specific embodiments of the invention, the essential ingredients of water, glycerin and polysorbate can be variously supplemented with further additives, including those illustratively mentioned hereinabove. In one embodiment, such additives include one or more of pathenol, cysteine, betasitosterol and retinol. In a further embodiment, two or more of such additives are incorporated in the carrier composition, and in other embodiments at least three of such components are present, with still other compositions including all four of such additives.

The carrier formulations of the invention may be constituted in a wide variety of forms, depending on the extent of evaporative loss and systemic migration associated with the active ingredient composition. Accordingly, the formulation of the invention may be readily empirically established for a particular active ingredient composition susceptible to such evaporative and systemic modes of loss, without undue experimentation, based on the disclosure herein.

In one illustrative embodiment of the invention, the carrier composition includes the following ingredients:

Water
Glycerin
Polysorbate 80
Retinol
Serenoa Serrulata Fruit Extract
Betasitosterol
Panthenol
Cystine
Biotin
Polysorbate 20
DMDM Hydantoin
Methylparaben The active ingredient(s) with which the carrier is useful include a wide variety of topical agents. One particularly preferred class of active ingredients comprises hair care and head care products, including hair growth promoters, hair damage rejuvenating agents, hair care cosmetic agents, scalp treatment products, shampoos, sunscreens and sun blocks, etc. One particularly preferred application for the carrier compositions of the present invention is as a vehicle for formulation of minoxidil, and application of the resulting minoxidil formulation to the scalp, as a hair growth promoter.

In such preferred application to minoxidil, the carrier composition of the present invention serves to neutralize the alcoholic properties of the minoxidil solution, so that the solution remains in liquid form for a longer period of time and does not penetrate the dermal tissue as rapidly.

In like manner, other alcoholic active ingredients and alcoholic compositions of active ingredient components can be neutralized for sustained presence/persistence on the body for purposes of therapeutic intervention, cosmetic enhancement, etc.

In general, the amount of minoxidil in the minoxidil-containing formulations of the invention incorporating the carrier composition may be at any suitable concentration, with concentration in the range of from about 0.1 weight percent to about 15 weight percent or more of minoxidil being generally useful, and with preferred concentrations of minoxidil in the formulation generally being on the order of from about 0.5 weight percent to 10 weight percent, based on the weight of the formulation. Other embodiments within the general scope of the invention utilize minoxidil in varying ranges, such as in a range of 1-7 wt %, 2-6 wt %, and 4-6 wt %, based on the total weight of the formulation.

The minoxidil-containing formulations of the invention may be employed as part of a continuing program of use of minoxidil, in which such formulations are applied to the scalp at regular intervals, as for example from twice a day, every day in an amount of 0.5-2 mL of the composition in each administration.

While the invention has been described herein with respect to particular aspects, features and embodiments, it will be recognized that the invention is not thus limited, and contemplates additional compositions, formulations, and methods of formulation and use, beyond the specific description herein. Accordingly, the invention is intended to be broadly construed, as including such variations, modifications and alternative embodiments as may readily suggest themselves to those of ordinary skill in the art, based on the disclosure herein.

What is claimed is:

1. A topical hair growth formulation, consisting of:
    an alcoholic active ingredient composition, wherein the active ingredient is minoxidil, in an amount of from 4-6 percent, based on total weight of the formulation;
    water in an amount of from 20-60 percent by weight, based on total weight of the formulation;
    glycerin, in an amount of from 6-20 percent by weight, based on total weight of the formulation; and
    polysorbate 80.

2. A composition comprising:
    an alcoholic active ingredient composition, wherein the active ingredient is minoxidil, in an amount of from 4-6 percent, based on total weight of the formulation;
    water in an amount of from 20-60 percent by weight, based on total weight of the formulation;
    glycerin, in an amount of from 6-20 percent by weight, based on total weight of the formulation; and
    polysorbate 80,
wherein the composition is administrable to the scalp and is effective to retard evaporative loss and systemic penetration of minoxidil.

* * * * *

UNITED STATES PATENT AND TRADEMARK OFFICE
CERTIFICATE OF CORRECTION

| | | |
|---|---|---|
| PATENT NO. | : 8,147,815 B2 | Page 1 of 1 |
| APPLICATION NO. | : 11/305647 | |
| DATED | : April 3, 2012 | |
| INVENTOR(S) | : Shane Malek | |

It is certified that error appears in the above-identified patent and that said Letters Patent is hereby corrected as shown below:

Column 2, lines 36-37: "...carrier composition suitable for use with active ingredients ingredient compositions..." should be -- carrier composition suitable for use with active ingredient compositions --.

Signed and Sealed this
Second Day of October, 2012

David J. Kappos
*Director of the United States Patent and Trademark Office*